United States Patent [19]

Ohyu

[11] Patent Number: 5,730,131
[45] Date of Patent: Mar. 24, 1998

[54] METHOD OF ESTIMATING BIOELECTRIC CURRENT SOURCE

[75] Inventor: Shigeharu Ohyu, Tochigiken, Japan

[73] Assignee: Kabushiki Kaisha Toshiba, Kawasaki, Japan

[21] Appl. No.: 546,322

[22] Filed: Oct. 20, 1995

[30] Foreign Application Priority Data

Oct. 31, 1994 [JP] Japan .................... 6-266577

[51] Int. Cl.$^6$ .................................... A61B 5/05
[52] U.S. Cl. .................. 28/653.1; 128/901; 128/731; 324/244; 324/248; 324/260
[58] Field of Search ............... 128/653.1, 731, 128/733, 901; 324/244, 248, 260, 263

[56] References Cited

U.S. PATENT DOCUMENTS

| | | | |
|---|---|---|---|
| 3,980,076 | 9/1976 | Wikswo | 128/2.05 F |
| 4,736,751 | 4/1988 | Gevins et al. | 128/732 |
| 4,974,602 | 12/1990 | Abraham-Fuchs et al. | 128/731 |
| 5,136,242 | 8/1992 | Abraham-Fuchs | 128/653.1 |
| 5,269,325 | 12/1993 | Robinson et al. | 128/653.1 |
| 5,601,081 | 2/1997 | Tomita et al. | 128/653.1 |
| 5,603,321 | 2/1997 | Kynor et al. | 128/653.1 |

OTHER PUBLICATIONS

Kensuke Sekihara et al. "The Use of Noise and Signal-Source Covariance Matrices in Reconstructing Biocurrent Distributions from Biomagnetic Measurements." SPIE vol. 1896 Physics of Medical Imaging, 1993, pp. 403–412.

*Primary Examiner*—Marvin M. Lateef
*Assistant Examiner*—Eleni Mantis Mercader
*Attorney, Agent, or Firm*—Oblon, Spivak, McClelland, Maier & Neustadt, P.C.

[57] ABSTRACT

A plurality of magnetic field measurement units are arranged near a patient, a current source distribution and/or a current dipole in the patient are estimated on the basis of plurality of magnetic field distribution data measured by the magnetic field measurement units within a predetermined period of time. In particular, the current distribution and the current dipole at the desired time within the predetermined period of time are estimated by using spatiotemporal magnetic field distribution data measured by the plurality of magnetic field measurement units within the predetermined period of time and correlation information of the spatiotemporal magnetic distribution data. The current distribution and the current dipole are estimated by using cross-correlation information of noise data measured by the plurality of magnetic field measurement units.

23 Claims, 9 Drawing Sheets

TIME SERIES OF
MAGNETIC FIELD
DISTRIBUTION

SPATIOTEMPORAL CORRELATION INFORMATION OF NOISE

PROFILE OF CURRENT DIPOLE

MEASUREMENT AND ASSUMPTION

ASSUMPTION

NONLINEAR OPTIMIZATION ALGORITHM → ESTIMATION VALUE OF POSITION AND TIME PROFILE OF CURRENT DIPOLE

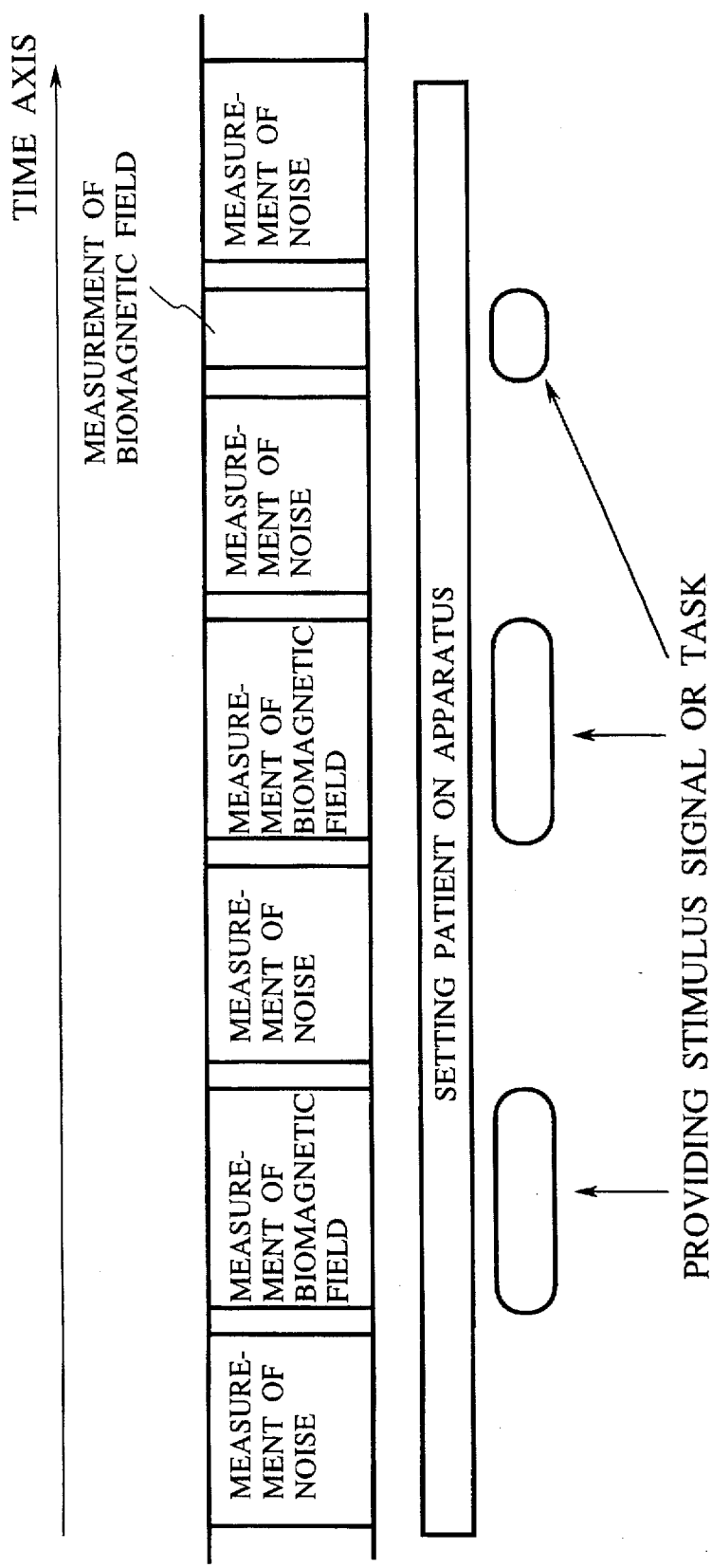

METHOD OF ESTIMATING BIOELECTRIC CURRENT SOURCE

BACKGROUND OF THE INVENTION

1. Field of Industrial Application

The present invention relates to a method of estimating a bioelectric current source in which a magnetic field outside an organism is measured, and a current source distribution in the organism is estimated on the basis of the measurement result.

2. Prior Art

In recent years, with the progress of a medical diagnostic apparatus, a bioelectric current source estimation apparatus for estimating a current source distribution or current dipole in an organism has been practically used. The bioelectric current source estimation apparatus has a plurality of SQUID (Superconducting QUantum Interference Device) flux meters arranged near a patient, and estimates a current source distribution or a current dipole in the organism on the basis of a magnetic field distribution estimated by the SQUID flux meters.

FIG. 1 is a block diagram showing the schematic arrangement of a general bioelectric current source estimation apparatus. A plurality of pickup coils 3 are arranged around a head 4 of a patient. A magnetic flux converged by each pickup coil 3 is measured by a SQUID flux meter 2 arranged for each pickup coil 3, and magnetic field data is output through a drive circuit 1.

As a conventional method of estimating a bioelectric current source distribution by using such a bioelectric current source estimation apparatus, an equivalent dipole method is known. This method will be described below.

Assume that a bioelectric current source distribution consists of a single current dipole or few current dipoles. In this case, it is known that the above problem can be relatively easily solved. A magnetic field distribution (magnetic fields at several points around a target region of an organism) at certain time is measured. A magnetic field distribution which should be generated outside the organism when it is assumed that a current dipole is located at a position in the organism is calculated. The position of the current dipole is moved such that a square error between the magnetic field obtained by the calculation and the measured magnetic field decreases. Finally, a position where the square error is minimum is set as an estimate position for the current dipole. That is, in order to estimate a current dipole at certain time, information of a magnetic field distribution at only the corresponding time is used.

However, when the number of assumed current dipoles is large, a measurement error, an error of a cranium model assumed when a magnetic field distribution is calculated, a positional error of a current dipoles which are to be estimated and are influenced by external noise coming from the outside of the organism becomes extremely large. It is actually difficult to estimate a large number of dipoles.

As another method, the following method is examined. That is, a bioelectric current source distribution by using a generalized inverse matrix (also called a pseudo inverse matrix) (Kullmann W. H., Jandt K. D., Schlitt H. A., Dallas W. J., Smith W. E., A linear estimation approach to biomagnetic imaging, ibid, 1989, 571–547) or singular value decomposition (Tchinardi U., Furuie S. S., Campos J. G., Melo C. P. ':The use of singular value decomposition in the analysis of the QKS. complex isofield maps., Biomagnetism'87, Tokyo Denki University Press Tokyo 1987, 330–333) on the basis of a result obtained by measuring a magnetic field distribution at certain time. In two-dimensional simulation, it was reported that the bioelectric current source distribution could be estimated to some extent. However, the actual bioelectric current source distribution cannot be easily estimated, since an actual organism has a three-dimensional current source distribution. This is because information obtained by measuring the magnetic field distribution is insufficient to perform three-dimensional estimation.

In this manner, the conventional method of estimating a bioelectric current source has the following drawbacks. That is, an estimation error increases in proportion to the number of dipoles in the equivalent dipole method, and the three-dimensional estimation cannot be easily performed in a method of performing estimation by using the generalized inverse matrix or the singular value decomposition.

SUMMARY OF THE INVENTION

The present invention has been made in consideration of the above circumstances, and has its object to provide a method of estimating a bioelectric current source in which estimation of a large number of dipoles or estimation of a distribution current can be performed at a high accuracy.

In order to achieve the above object, the present invention provides a method of estimating a bioelectric current source in which a plurality of magnetic field measurement means are arranged near a patient, and a current source distribution and/or a current dipoles in the patient on the basis of a magnetic field distribution measured by the magnetic field estimation means, comprising the step of: estimating a current distribution and/or a current dipole at desired time within a predetermined period of time by using a plurality of magnetic field distribution data measured within the predetermined period of time.

According to a preferred embodiment of the present invention, spatiotemporal magnetic field distribution data measured by said plurality of magnetic field measurement means within the predetermined period of time and temporal correlation information and spacial correlation information of the spatiotemporal magnetic distribution data are used to estimate the current distribution and/or the current dipole at the desired time within the predetermined period of time.

According to another embodiment of the present invention, on the basis of correlation information of a bioelectric current source obtained by said plurality of magnetic field distribution data measured within the predetermined period of time and a single magnetic field distribution data of the plurality of magnetic field distribution data, a position of a single current dipole or positions of a plurality of current dipoles at time at which the single magnetic field distribution data is measured is/are estimated.

In this manner, since a position where a dipole is apt to be located can be provided in estimation of a dipole position, estimation accuracy of a dipole position can be improved.

According to still another embodiment of the present invention, spatiotemporal current distributions within the predetermined period of time are simultaneously estimated on the basis of the spatiotemporal magnetic distribution data measured by said plurality of magnetic field measurement means within the predetermined period of time.

In this manner, since the temporal and spatial resolutions of the estimated current source distributions can be limited to arbitrary distributions, an estimation result can be stabilized.

According to still another embodiment of the present invention, approximating a current source in the patient by a current dipole, assuming a change in the current dipole with time as a profile described in a predetermined parameter, and estimating the position, generation time, direction, maximum amplitude, and time profile of the current dipole by using the spatiotemporal magnetic field distribution data measured by said plurality of magnetic field measurement means within the predetermined period of time.

In this manner, since a plurality of samples are used as the measurement values of magnetic field distributions used for estimation, an amount of information which can be used to estimate current dipoles increases, and an increase in the number of parameters related to the plurality of current dipoles subjected to estimation is not larger than the increase in the amount of information. For this reason, the positions, directions, magnitudes of the current dipoles .and changes in magnitude of the current dipoles with time can be estimated stably more than in the prior art.

According to still another embodiment of the present invention, setting a plurality of evaluation points in a desired region in the patient to assume that current dipoles are respectively present at the evaluation points, expressing changes in the components of current dipole moments at the evaluation points with time by parameters smaller in number than the number of temporal magnetic field distribution data measured within the predetermined period of time, and estimating the changes with time on the basis of the temporal magnetic field distribution data.

In this manner, since the number of parameters to be estimated can be reduced, estimation values can be stably obtained, although the temporal resolutions of the estimated current dipoles are consequently limited.

The nature, principle and utility of the invention will become more apparent from the following detailed description when read in conjunction with the accompanying drawings.

BRIEF DESCRIPTION OF THE DRAWINGS

In the accompanying drawings:

FIG. 11 is a timing chart showing other timings of noise estimation.

DESCRIPTION OF THE PREFERRED EMBODIMENTS

Embodiments of the present invention will be described below with reference to the accompanying drawings.

Figure 1:
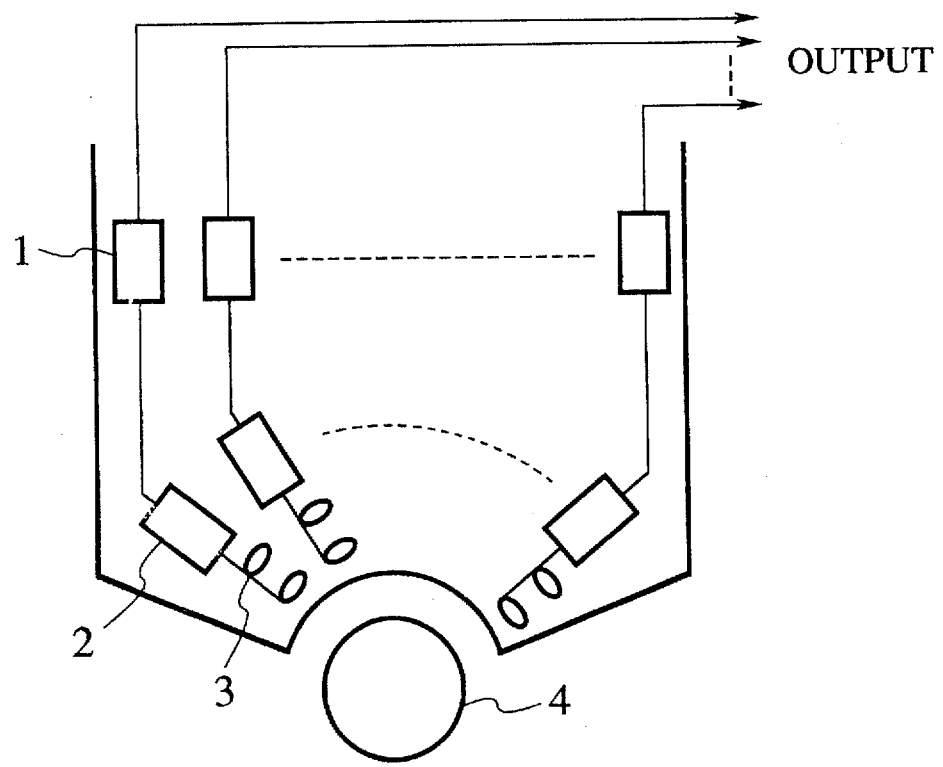
FIG. 1 is a block diagram showing the schematic arrangement of a conventional, general bioelectric current source estimation apparatus.
Figure 2:
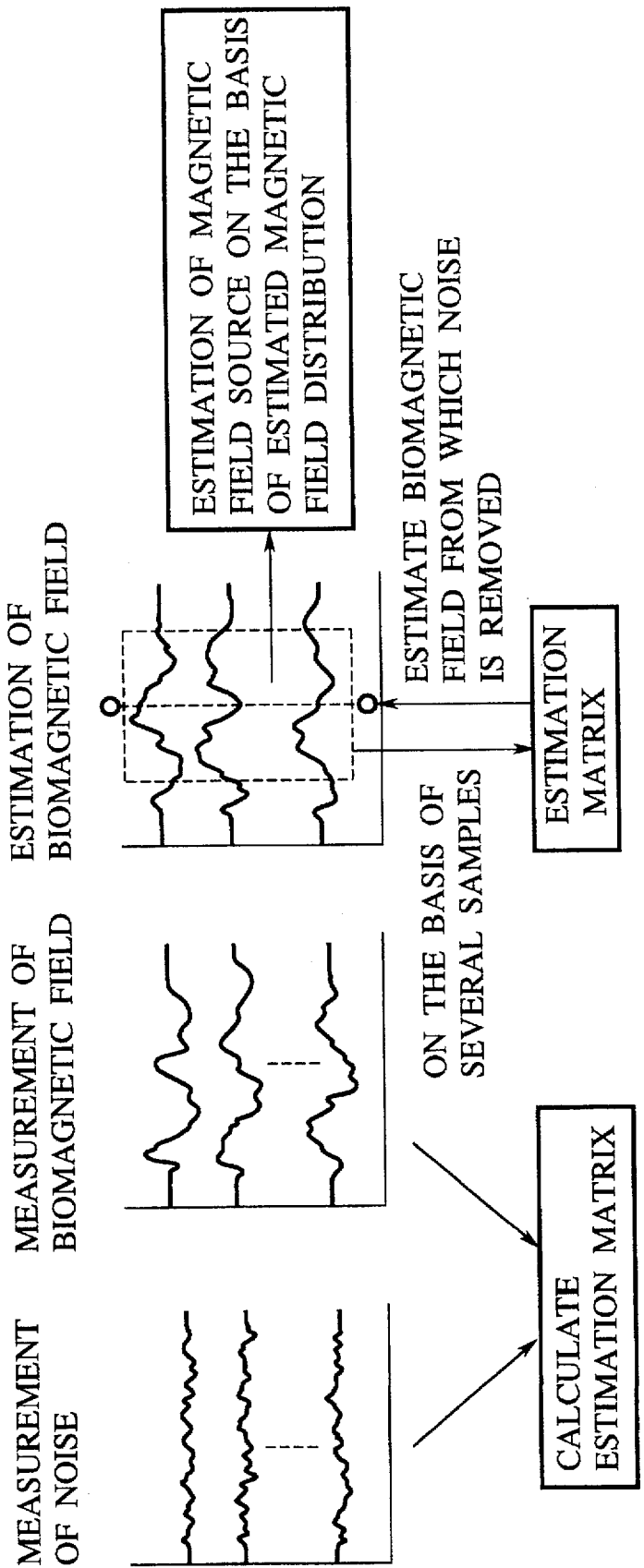
FIG. 2 is a conceptual view showing the first embodiment in a method of estimating a bioelectric current source according to the present invention.

FIG. 2 is a conceptual view showing the first embodiment in a method of estimating a bioelectric current source according to the present invention. As shown in FIG. 2, according to the present invention, on the basis of measurement data at time of interest in biomagnetic field measurement data to which noise is added and several measurement data before and after the measurement data at the time of interest, the estimation value of a magnetic field distribution (true magnetic field distribution from which noise is removed) at the time of interest is calculated. On the basis of the information of the magnetic field distribution obtained as described above, a current dipole and a current source distribution are estimated by a conventional, general method. In particular, spatiotemporal correlation information of noise and spatiotemporal correlation information of measurement data are used to obtain an optimum estimation matrix for estimating the true magnetic field distribution.

The measurement data of the jth sample of the ith channel of a magnetic field distribution measured by a channel number M is represented by $\Phi_{i,j}$. Samples of magnetic field distributions used for estimation are $L^-$ sample at time before time at which estimation is to be performed, $L^+$ sample at time after the time at which estimation is to be performed, and one sample corresponding to the time at which estimation is to be performed, and the sum $L=L^-+L^++1$ samples is set. The range of the second subscript of the measurement value $\Phi_{i,j}$ i.e., j, is set to be the range of $-L^-$ to $L^+$, and a subscript corresponding to the sample at time at which the estimation is to be performed is set to be 0(zero). It is assumed that the measurement data $\Phi_{i,j}$ can be expressed by the sum of a true value $\Phi_{i,j}{}^s$ and noise $\Phi_{i,j}{}^n$ as shown in expression (1).

$$\Phi_{i,j}=\Phi_{i,j}{}^s+\Phi_{i,j}{}^n \tag{1}$$

A vector obtained by vertically arranging $\Phi_{i,j}$ such that j changes from $-L^-$ to $L^+$ is represented by $\Phi_i$, and a vector obtained by vertically arranging $\Phi_i$ such that i changes from i to M is represented by $\Phi$. When $\Phi_i{}^s$, $\Phi_n$, $\Phi^n$, and $\Phi_n$ are defined with respect to $\Phi_{i,j}{}^s$ and $\Phi_{i,j}{}^n$ like $\Phi_{i,j}$, expression (1) can be expressed as follows.

$$\Phi=\Phi_s+\Phi_n \tag{2}$$

In this case, an estimation value $\hat{\Phi}_{i,0}$ of $\Phi_{i,0}$ can be expressed by the following expression.

$$\begin{aligned}\Phi_{i,0} &= <\Phi_{i,0}^s\Phi^s><\Phi\Phi^t>^{-1}\Phi \\ &= <\Phi_{i,0}^s\Phi_s^t><\Phi\Phi^t>^{-1}\Phi\end{aligned} \tag{3}$$

In this case, $<\Phi_{i,0}{}^s \Phi^t>$ is a correlation matrix of $\Phi_{i,0}{}^s$ and 1×LM of $\Phi$, $<\Phi_{i,0}{}^s \Phi_s{}^t>$ is a correlation matrix of $\Phi_{i,0}{}^s$ and 1×LM of $\Phi_s$, and $<\Phi\Phi^t>$ is an autocorrelation matrix of LM×LM of $\Phi$. Expression (3) is transformed on the assumption that noise and a signal are orthogonal.

Although estimation itself is performed by expression (3), $<\Phi_{i,0}{}^s \Phi_s{}^t>$ or $<\Phi\Phi^t>$ and an estimation matrix $<\Phi_{i,0}{}^s \Phi_s{}^t><\Phi\Phi^t>^{-1}$ must be constituted prior to the estimation. When $<\Phi\Phi^t>$ is divided in detail, $<\Phi\Phi^t>$ can be expressed as shown in expression (4):

$$\langle \Phi \Phi' \rangle = \left\langle \begin{pmatrix} \Phi_1 \\ \cdot \\ \cdot \\ \cdot \\ \Phi_M \end{pmatrix} (\Phi_1' \ldots \Phi_M') \right\rangle = \quad (4)$$

$$\begin{pmatrix} \langle \Phi_1 \Phi_1' \rangle & \ldots & \langle \Phi_1 \Phi_M' \rangle \\ \cdot & & \cdot \\ \cdot & & \cdot \\ \cdot & & \cdot \\ \langle \Phi_M \Phi_1' \rangle & \ldots & \langle \Phi_M \Phi_M' \rangle \end{pmatrix}$$

Each element of the matrix on the left-hand side is the cross-correlation matrix of $\Phi_i$ and $\Phi_j$ (i, j=1 ... M). When time series obtained by adding the measurement values of k samples to $\Phi_i$ and $\Phi_j$ are represented by $a_h$ and $b_h$ (h=−L⁻ ... L⁺+k), expression (6) is obtained by using a cross-correlation function $R_l^{i,j}$ between $\Phi_i$ and $\Phi_j$ calculated by expression (5):

$$R_l^{i,j} = \sum_{h=0}^{k-1} a_{h+l} b_h \text{ for } l = -L^- \ldots L^+ \quad (5)$$

$$\langle \Phi_i \Phi_j' \rangle = \begin{pmatrix} R_0^{ij} & R_1^{ij} & \ldots & R_L^{ij} \\ R_1^{ij} & R_0^{ij} & & \\ \cdot & & \cdot & \\ \cdot & & & \cdot \\ \cdot & & & \cdot \\ R_L^{ij} & & \ldots & R_0^{ij} \end{pmatrix} \quad (6)$$

These expressions are synthesized with each other by using expression (4), thereby constituting $\langle \Phi \Phi' \rangle$. On the other hand, $R_l^{i,j}$ can also be obtained by expression (7).

$$R_l^{i,j} = D^{-1}[D[a_h]D^*[b_h]] \quad (7)$$

where D is an operator for performing discrete Fourier transform, $D^{-1}$ is an operation for performing a discrete inverse Fourier transform, and * is the sign of a complex conjugate. In this case, the k samples are added to $a_h$ and $b_h$, and L 0s must be added to the $a_h$ and $b_h$. $R_{l+2L+k}^{i,j}$ obtained by adding 2L+k is assigned to $R_l^{i,j}$ with a negative subscript. Calculation can be performed at a high speed by using expression (7) than by using expression (5).

When $\langle \Phi_{i,0}^s \Phi_s^t \rangle$ is divided, the following expressions can be obtained:

$$\langle \Phi_{i,0}^t \Phi_s^t \rangle = (\langle \Phi_{i,0}^t \Phi_1^t \rangle \ldots \langle \Phi_{i,0}^t \Phi_M^t \rangle) \quad (8)$$

$$\langle \Phi_{i,0}^t \Phi_j^t \rangle = (R_{-L}^{ij} \ldots R_{L^+}^{ij}) \quad (9)$$

In this case, $R_l^{si,j}$ is a correlation function between the signal component of the ith channel and the signal component of the jth channel, and can be calculated by expression (10) on the assumption that a signal is independent of noise.

$$R_l^{si,j} = R_l^{i,j} - R_l^{ni,j} \quad (10)$$

$R_l^{ni,j}$ is a correlation function between the ith and jth channels of noise. When the time series of the ith and jth channels are extracted from a measurement value obtained when only noise is measured in the state wherein no patient is set in the apparatus (or a patient is set in the apparatus, but no target signal is not generated by the organism), and these time series are represented by $a_h$ and $b_h$, $R_l^{ni,j}$ can be formally expressed by expression (11):

$$R_l^{ni,j} = D^{-1}[D[a_h]D^*[b_h]] \quad (11)$$

That is, $R_l^{ni,j}$ can be obtained by performing inverse Fourier transform to the power spectrum of noise. L or more 0s must be added to $a_h$ and $b_h$. At this time, the power spectrum $D[a_h]D^*[b_h]$ of noise is not a value obtained by calculation. A smooth curve or an addition means obtained by performing measurement and calculation several times is preferably used as the power spectrum $D[a_h]D^*[b_h]$ of noise. As in calculation of the correlation function $R_l^{i,j}$ of the measurement value, a smooth curve is preferably used as $D[a_h]D^*[b_h]$, or an addition means is preferably calculated.

On the basis of $\langle \Phi_{i,0}^s \Phi_s^t \rangle$, $\langle \Phi \Phi' \rangle$, and, the measurement value $\Phi$, the estimation value of a magnetic field distribution at time at which estimation is to be performed is obtained by expression (3). Thereafter, by using the resultant estimation value, estimation of a single current dipole or a plurality of current dipoles or estimation of a distribution current are performed by a normal method.

Note that an estimation matrix $\langle \Phi_{i,0}^s \Phi_s^t \rangle \langle \Phi \Phi' \rangle^{-1}$ need not be changed unless the statistical characters of noise and a biomagnetic field largely change. For this reason, for example, calculation is preferably performed once for a series of induced magnetic fields to which the same stimulus and task are applied. The resultant estimation matrix can be applied to all the time series of the series of induced magnetic fields.

Figure 3:
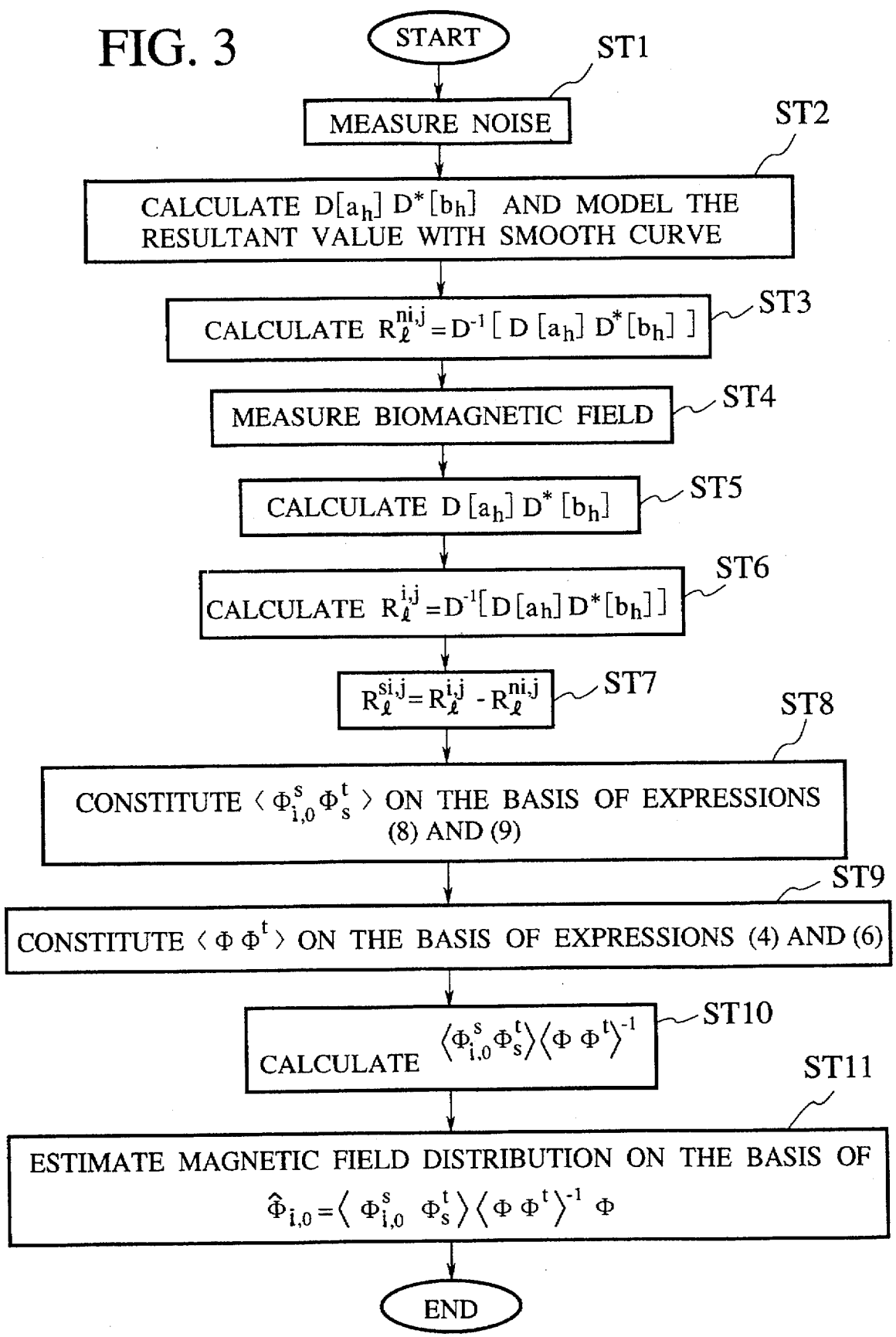
FIG. 3 is a flow chart showing a processing procedure of the first embodiment.

FIG. 3 is a flow chart showing a processing procedure of the first embodiment. Referring to FIG. 3, in step 1, in the state wherein no patient is set in the apparatus to measure noise or wherein a patient is set in the apparatus but a stimulus or a task is applied to the patient to measure an induced magnetic field, the time series of an M-channel magnetic field are measured.

Figure 4:
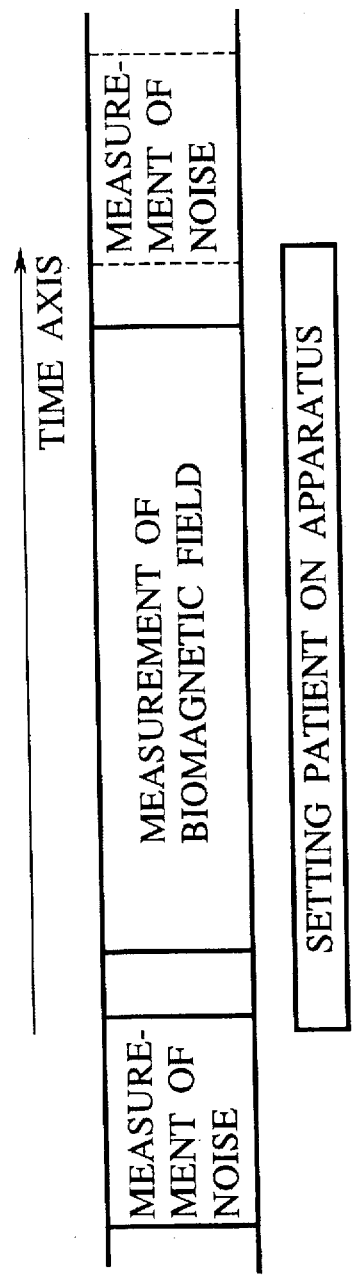
FIG. 4 is a timing chart showing timings of noise estimation.

Note that noise may be actually measured, as shown in FIG. 4, prior to measure of a biomagnetic field, i.e., at the time of starting up the apparatus, immediately before the measurement of the biomagnetic field, or, as indicated by a dotted line in FIG. 4, after the measurement of the biomagnetic field. The noise measurement may be performed by another method (to be described later).

In step 2, the data of the ith channel of a measured magnetic field is represented by $a_h$, the data of the jth channel is represented by $b_h$, $D[a_h]D^*[b^h]$ of all combinations are calculated by using a fast Fourier transform algorithm, and the calculation result is modeled by a smooth curve.

In step 3, $D[a_h]D^*[b^h]$ obtained as described above is subjected to a discrete inverse Fourier transform by using the fast Fourier transform algorithm to obtain $R_l^{ni,j}$.

In step 4, a patient is set in the apparatus, and M-channel time series data are measured.

In step 5, data of an L sample are extracted from the measured M-channel biomagnetic field measurement data, the data of the ith channel is represented by $a_h$, and the data of the jth channel is represented by $b_h$, and $D[a_h]D^*[b^h]$ of all the combinations are calculated.

In step 6, $D[a_h]D^*[b^h]$ obtained as described above is (modeled by a smooth curve as needed) subjected to discrete inverse Fourier transform by using the fast Fourier transform algorithm to obtain $R_l^{i,j}$.

In step 7, $R_l^{si,j}$ is obtained on the basis of $R_l^{ni,j}$ obtained in step 3 and $R_l^{i,j}$ obtained in step 6.

In step 8, $\langle \Phi_{i,0}^s \Phi_s^t \rangle$ is constituted by expressions (8) and (9).

In step 9, $\langle \Phi \Phi' \rangle$ is constituted by expressions (4) and (6).

In step 10, $\langle \Phi_{i,0}^s \Phi_s^t \rangle \langle \Phi \Phi' \rangle^{-1}$ is calculated to obtain an estimation matrix.

In step 11, a magnetic field distribution at time at which estimation is to be performed is estimated by $\Phi_{i,0=<\Phi i,0}{}^s$ $\Phi_s{}^t><\Phi\Phi^t>^{-1} \Phi$.

As described above, since the optimum estimation value of the magnetic field distribution at time at which estimation is to be estimated is obtained, estimation of a single dipole or a plurality of dipoles or estimation of a distribution current are performed by a known method by using the optimum estimation value. In this manner, according to the first embodiment, the spatiotemporal dependency of the measurement value and noise are considered in estimation of a bioelectric current source, and the bioelectric current source can be estimated such that the influence of noise is minimized. For this reason, the estimation accuracy of the bioelectric current source is improved.

Figure 5:
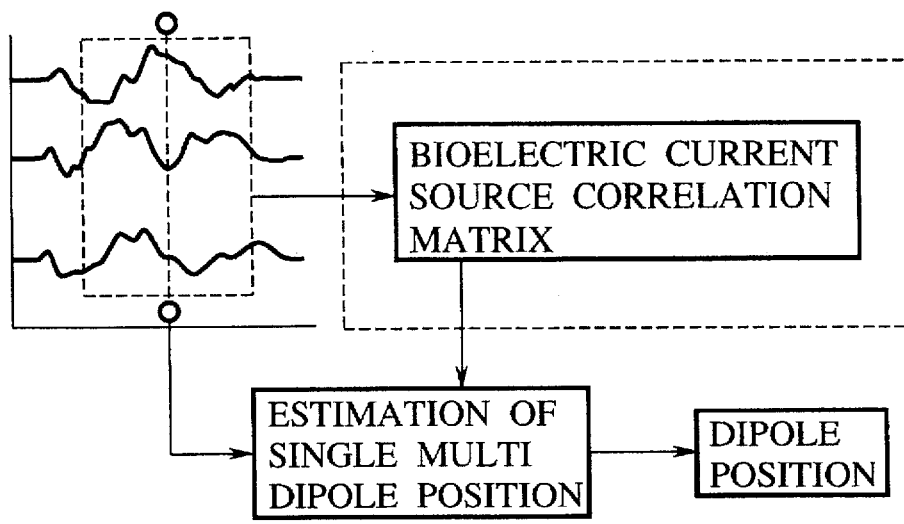
FIG. 5 is a conceptual view showing the second embodiment in a method of estimating a bioelectric current source according to the present invention.

The second embodiment of the present invention will be described below. FIG. 5 is a conceptual view showing the second embodiment in a method of estimating a bioelectric current source according to the present invention. As shown in FIG. 5, according to the second embodiment, on the basis of the correlation matrix of the bioelectric current source obtained by the magnetic field distribution measurement data of the L sample and the measurement data of the magnetic field distribution of a single sample, a single current dipole position or a plurality of current dipole positions at time corresponding to the single sample are estimated.

A vector obtained by vertically arranging the measurement values $\Phi_{i,j}$ of the jth sample of the ith channel of the magnetic field distribution measured at the number M of channels such that i changes from 1 to M is represented by $\Psi_j$, and a vector obtained by vertically arranging $\Psi_j$ such that j changes from $-L^-$ to $L^+$ is represented by $\Psi$. When $\Psi_j{}^s$, $\Psi_s$, $\Psi_j{}^n$, and $\Psi_n$ are defined with respect to $\Phi_{i,j}{}^s$ and $\Phi_{i,j}{}^n$ like $\Phi_{i,j}$, expression (1) can be expressed as follows.

$$\Psi = \Psi_s + \Psi_n \quad (12)$$

Assuming that N evaluation points are distributed in a target area of an organism, and current dipoles are respectively present at the evaluation points, the bioelectric current source distribution is expressed. A moment at time corresponding to the jth sample of a current dipole present at the ith evaluation point is represented by $J_{i,j}$. In addition, a vector obtained by vertically arranging N current dipole moments at the evaluation points is represented by $J_j$. Assuming that the magnetic field distribution $J_j$ of the jth sample and the magnetic field distribution $\Psi_j{}^s$ have a linear relationship, the relationship between the magnetic field distributions can be expressed by using an M×3 N matrix B as follows:

$$\Psi_j{}^s = BJ_j \quad (13)$$

By using the matrix B, an correlation matrix $<J_jJ_j{}^t>$ of the bioelectric current source is expressed as follows:

$$<J_jJ_j{}^t> = B^+(<\Psi_j\Psi_j{}^t> - <\Psi_j{}^n\Psi_n{}^t>)B^{+t} \quad (14)$$

where $B^+$ is a Moor-Penrose general inverse matrix. When M<3 N, $B^+$ is given by expression (15).

$$B^+ = B^t(BB^t)^{-1} \quad (15)$$

When ergodicity is assumed, $<\Psi_j\Psi_j{}^t>$ and $<\Psi_j{}^n\Psi_j{}^n>$ of all the samples have the same value, and can be obtained by a time mean as follows:

$$<\Psi_j\Psi_j{}^t> \equiv \frac{1}{L^- + L^+ + 1} \sum_{k=-L^-}^{L^+} \Psi_k\Psi_k{}^t \quad (16)$$

$$<\Psi_j{}^n\Psi_j{}^n{}^t> \equiv \frac{1}{L^- + L^+ + 1} \sum_{k=-L^-}^{L^+} \Psi_k{}^n\Psi_k{}^{nt} \quad (17)$$

When $R_0{}^{i,j}$ and $R_0{}^{n i,j}$ obtained by expressions (7) and (11) are used, $<\Psi_j\Psi_j{}^t>$ and $<\Psi_j{}^n\Psi_j{}^n>$ can be obtained by the following expressions:

$$<\Psi_j\Psi_j{}^t> = \begin{pmatrix} R_0^{0,0} & \cdots & R_0^{M,0} \\ \vdots & & \vdots \\ R_0^{0,M} & & R_0^{M,M} \end{pmatrix} \quad (18)$$

$$<\Psi_j{}^n\Psi_j{}^n{}^t> = \begin{pmatrix} R_0^{n0,0} & \cdots & R_0^{nM,0} \\ \vdots & & \vdots \\ R_0^{n0,M} & & R_0^{nM,M} \end{pmatrix} \quad (19)$$

$<J_jJ_j{}^t>$ obtained as described above has the same value with respect to all js.

$<J_jJ_j{}^t>$ is expressed by expression (20) on the basis of the definition of $<J_jJ_j{}^t>$.

$$<J_jJ_j{}^t> = \begin{pmatrix} <J_{j,1}J_{j,1}{}^t> & \cdots & <J_{j,1}J_{j,N}{}^t> \\ \vdots & & \vdots \\ <J_{j,N}J_{j,1}{}^t> & \cdots & <J_{j,N}J_{j,N}{}^t> \end{pmatrix} \quad (20)$$

Each element $<J_{i,j} J_{j,k}{}^t>$ in the matrix expresses the correlation between the dipole moments at the evaluation points i and k. However, when interpolation such as linear interpolation is performed, the correlation between the dipole moments at arbitrary points can be approximately obtained.

Assume that the correlation between dipole moments present a points $x_1$ and $x_2$ is represented by R ($x_1$, $x_2$).

By using K($x_1$, $x_2$) obtained as described above, the positions of a plurality of dipoles at time corresponding to the jth sample are estimated as follows. Assume that the number of dipoles to be estimated is represented by d. Each dipole position is represented by $r_i$ (i=1, ..., d), and each dipole moment is represented by $P_i$ (i=1, ..., d). For descriptive convenience, vectors obtained by vertically arranging the dipole positions and the dipole moments are represented by r and P. On the basis of R($x_1$, $x_2$) obtained above, a correlation matrix $R_{pp}$ between the components of the vector P is constituted as follows:

$$R_{PP}(r) = \begin{pmatrix} R(r_1, r_1) & \cdots & R(r_1, r_d) \\ \vdots & & \vdots \\ R(r_d, r_1) & \cdots & R(r_d, r_d) \end{pmatrix} \quad (21)$$

A magnetic field distribution $\Psi_j{}^s$ at which N dipoles expressed by the position r and the dipole moment P at the time corresponding to the jth sample is the function of the dipole position r and the moment P. However, the magnetic field distribution $\Psi_j{}^s$ can be expressed as follows by using a matrix A depending on the dipole position r, since the linear relation between the dipole moment and the magnetic field distribution is established.

$$\Psi_j{}^i(r,P) = A(r)P \qquad (22)$$

In this case, a matrix G is defined as follows:

$$G = (R_{pp}(r)^{-1} + A^t R_{\epsilon\epsilon}{}^{-1} A)^{-1} A^t R_{\epsilon\epsilon}{}^{-1} \qquad (23)$$

where $R_{\epsilon\epsilon}$ is the inter-channel correlation matrix of measured noise, and $R_{pp}$ is a correlation matrix between the components of the dipole moment P expressed by expression (21). Note that, if $R_{\epsilon\epsilon}$ is not well known, the matrix G may be replaced with the Moor-Penrose general inverse matrix of the matrix A.

In order to estimate the positions of d current dipoles assumed in a target region of an organism, r which minimizes the following evaluation function is calculated by various well-known nonlinear optimization algorithms.

$$S(r) = \frac{1}{2} (\Psi_i - \Psi_i{}^j(r, G\Psi_i))^t R_{\epsilon\epsilon}^{-1} (\Psi_i \Psi_i{}^j(r, G\Psi_i)) + \qquad (24)$$

$$\frac{1}{2} (G\Psi_i)^t R_{PP}(r)^{-1} (G\Psi_i) - \log \frac{1}{(2\pi)^{N/2} |R_{PP}(r)|^{1/2}}$$

However, the positions of the dipoles obtained by the above evaluation function tends to be obtained as a position shall lower than the actual position. In this case, the dipole position is obtained by using an evaluation function in which the second term of the right-hand side is neglected.

In this manner, according to the second embodiment, a position at which a dipole is apt to be located is given in estimation of a dipole position, the estimation accuracy of the dipole position is improved.

The third embodiment in a method of estimating a bioelectric current source according to the present invention will be described below.

Figure 6:
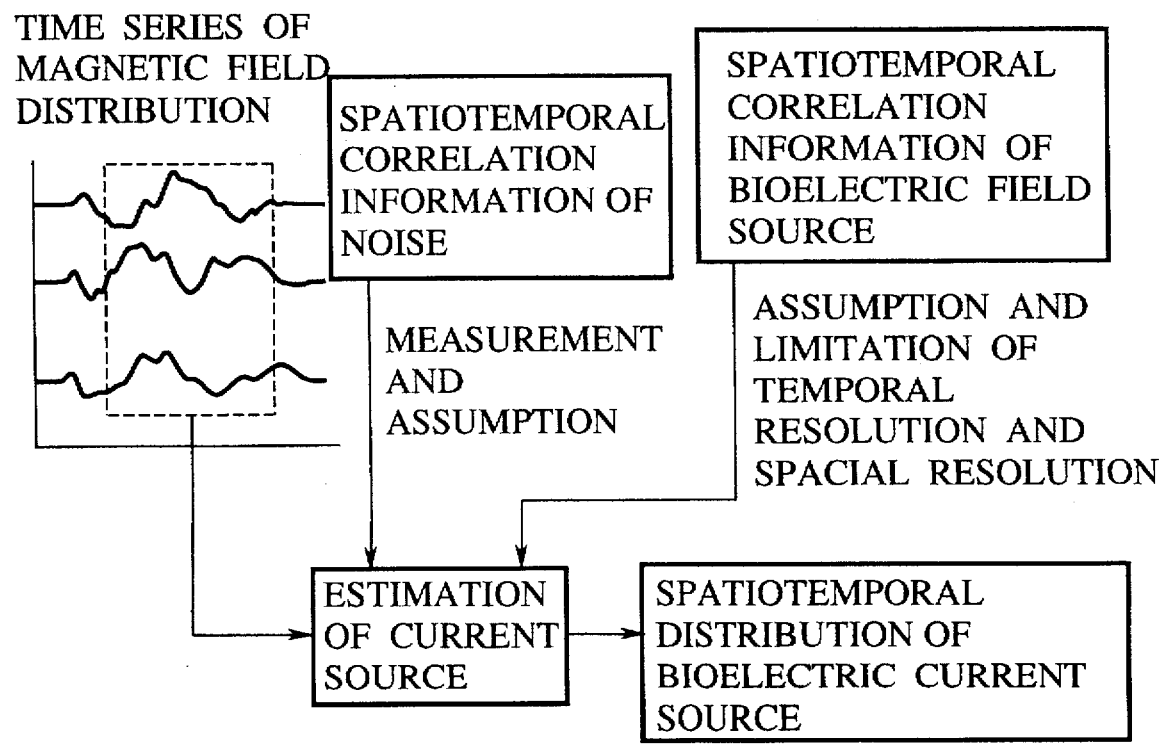
FIG. 6 is a conceptual view showing the third embodiment in a method of estimating a bioelectric current source according to the present invention.

FIG. 6 is a conceptual view of the third embodiment. According to this embodiment, on the basis of a time series, in a certain period of time, of the spacial distribution of a measured magnetic field, the time series of the spacial distribution of a cerebro-electric current source in the period of time are simultaneously estimated. In this case, when the spatiotemporal correlation information of measurement noise is obtained, the influence of the measurement noise can be reduced. When the spatiotemporal correlation information of the bioelectric current source is obtained, the spatial and temporal resolutions of the estimated current source distribution can be limited to arbitrary values. For this reason, an estimation result can be stably obtained.

<Constitution of Noise Correlation Matrix>

A noise correlation matrix $R_{nn}$ is constituted as follows on the basis of $R_l^{ni,j}$ described in the first embodiment.

$$<\Phi_i{}^t \Phi_j{}^t> = \begin{pmatrix} R_0^{ni,j} & R_1^{ni,j} & \cdots & R_L^{ni,j} \\ R_1^{ni,j} & R_0^{ni,j} & & \\ \vdots & & \ddots & \\ R_L^{ni,j} & & \cdots & R_0^{ni,j} \end{pmatrix} \qquad (25)$$

$$R_{nn} = <\Phi_n \Phi_n{}^t> = \begin{pmatrix} <\Phi_1{}^t \Phi_1{}^t> & \cdots & <\Phi_1{}^t \Phi_M{}^t> \\ \vdots & & \vdots \\ <\Phi_M{}^t \Phi_1{}^t> & \cdots & <\Phi_M{}^t \Phi_M{}^t> \end{pmatrix} \qquad (26)$$

<Constitution of Current Source Correlation Matrix>

On a frequency axis, the power spectrum of a current source is set. For example, the rectangular power spectrum of a cutoff frequency $f_c$ is set. This power spectrum is subjected to a discrete inverse Fourier transform to obtain the autocorrelation function of the current source. The autocorrelation function of the current source corresponding to 1-sample delay is represented by $R_1{}^J$. By using $R_1{}^J$, an autocorrelation matrix in the temporal direction of the current source is constituted as follows:

$$R^J = \begin{pmatrix} R_0^J & R_{-1}^J & \cdots & R_{-L}^J \\ R_1^J & R_0^J & & \\ \vdots & & \ddots & \\ R_L^J & & \cdots & R_0^J \end{pmatrix} \qquad (27)$$

A cutoff frequency $f_x$ in the spacial direction of the current source is set, and the rectangular power spectrum of the cutoff frequency $f_x$ is set. When the power spectrum is subjected to inverse Fourier transform, the following function is obtained:

$$s(x) = a^2 \frac{\sin(2\pi f_x x)}{2\pi f_x x} \qquad (28)$$

where a is a constant related to an amplitude. In this case, the representative magnitude of a dipole moment is given as the value of a.

The distance between the ith and jth evaluation points of a large number (N) of evaluation points set in a target region of an organism is set to be $d_{i,j}$. The correlation matrix $R_{JJ}$ of the current source obtained in consideration of both the temporal and spacial directions is constituted as follows:

$$R_{JJ} = (JJ^t) = \begin{pmatrix} s(d_{1,1})R^J & \cdots & s(d_{1,M})R^J \\ \vdots & & \vdots \\ s(d_{N,1})R^J & \cdots & s(d_{M,M})R^J \end{pmatrix} \qquad (29)$$

<Constitution of Transfer Matrix C>

An L×L matrix having, as a diagonal element, an i,j element $B_{i,j}$ of the M×3 N matrix B defined in the second embodiment is represented by $C_{i,j}$ as shown in expression (30).

$$C_{i,j} = \begin{pmatrix} B_{i,j} & & 0 \\ & \ddots & \\ 0 & & B_{i,j} \end{pmatrix} \qquad (30)$$

An LM×L3 N matrix having $C_{i,j}$ as an i,j element is defined as shown in expression (31).

$$C = \begin{pmatrix} c_{1,1} & \cdots & c_{1,N} \\ \vdots & & \vdots \\ \vdots & & \vdots \\ c_{M,1} & \cdots & c_{M,N} \end{pmatrix} \quad (31)$$

In this manner, a spatiotemporal distribution J of the current source in the target region of the organism and a spatiotemporal distribution $\Phi$ of a magnetic field in the target region are expressed as shown in expression (32) by using the transfer matrix C from J to $\Phi$.

$$\Phi = CJ \quad (32)$$

When a dipole moment corresponding to the jth sample at the ith evaluation point is represented by $J_{i,j}$ and a vector obtained by vertically arranging $J_{i,j}$ such that j changes from $-L^-$ to $L^+$ is represented by $J^i$, the distribution J defined as described above is a vector obtained by arranging $J^i$ such that i changes from 1 to N.

<Estimation of Current Source Distribution in Target Region of Organism>

By using the noise correlation matrix $R_{nn}$, the current source correlation matrix $R_{JJ}$ constituted as described above, and the measured magnetic field distribution $\Phi$, the current source distribution J in the target region of the organism is estimated.

$$J = R_{JJ}C^t(CR_{JJ}C^t + R_{nn})^{-1}\Phi \quad (33)$$

According to the third embodiment, the time series of the spatial distribution of a cerebro-electric current source in the same period of time are simultaneously estimated on the basis of the time series in a period of time in the spatial distribution of a measured magnetic field. In this case, when the spatiotemporal correlation information of the bioelectric current source is obtained, the temporal and spacial resolutions of the estimated current source distribution can be limited to arbitrary values. For this reason, an estimation result can be stably obtained. In addition, when the spatiotemporal correlation information of measurement noise is obtained, the influence of the measurement noise can be reduced.

Figure 7:
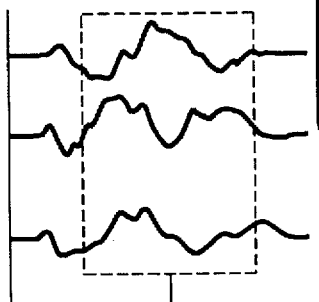
FIG. 7 is a conceptual view showing the fourth embodiment in a method of estimating a bioelectric current source according to the present invention.

The fourth embodiment in a method of estimating a bioelectric current source according to the present invention will be described below. FIG. 7 is a conceptual view of the fourth embodiment. According to this embodiment, as shown in FIG. 7, a change in bioelectric current dipole with time is assumed by a profile described in several parameters, and the position, generation time, maximum amplitude, and time profile of a single bioelectric current dipole or each of a plurality of bioelectric current dipoles are estimated on the basis of the time series of the measured magnetic field distribution.

Figure 8:
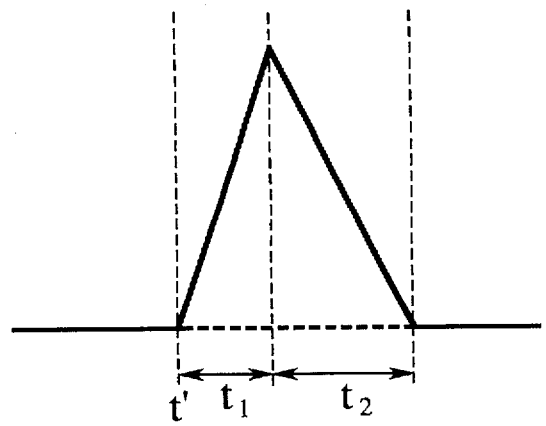
FIG. 8 is a graph showing a time profile assumed as a change in bioelectric current dipole with time.

As an example, a profile of the current dipole is assumed as shown in FIG. 8. FIG. 8 shows the time transition of the magnitude of a single dipole. Referring to FIG. 8, the maximum amplitude is obtained when a time $t_1$ has elapsed after the dipole is generated at time t', and the dipole is eliminated when a time $t_2$ has elapsed. At this time, a vector which expresses the generation time and profile of a dipole are defined:

$$\begin{pmatrix} t' \\ \log(t_1) \\ \log(t_2) \end{pmatrix} \quad (34)$$

Assume that the number of dipoles to be estimated is set to be N, and that the time profile of the ith dipole is represented by $t_i$. Similarly, assume that the position of the ith dipole is represented by $r_i$, and that a vector obtained by vertically arranging the maximum amplitudes of the three components of the ith dipole is represented by $P_i$.

It is considered that the positions $r_i$, maximum amplitudes $P_i$, and time profiles $t_i$ of N current dipoles are estimated on the basis of the time series $\Phi$ of the measured magnetic field distribution and the noise correlation matrix $R_{nn}$ of the magnetic field distribution. For descriptive convenience, a vector obtained by vertically arranging the positions $r_i$ of the N dipoles is represented by r, a vector obtained by vertically arranging the maximum amplitudes $P_i$ is represented by P, and a vector obtained by vertically arranging the time profiles $t_i$ is represented by t. When (the time series of) a magnetic field distribution generated by N dipoles which are described in the parameters such as position r, maximum amplitude P, and time profile t is set to be $\Phi^s(r,t,P)$, the $\Phi^s(r,t,P)$ can be expressed as follows by using the matrix A.

$$\Phi^s(r,t,P) = A(r,t) \quad (35)$$

When the measurement value $\Phi$ is given, P which minimizes a square error is given by:

$$P = G\Phi^s \quad (36)$$

where G is the general inverse matrix of the matrix A.

Assume that r and t which minimize the following evaluation function are used as the estimation values of the positions and time profiles of the N dipoles.

$$S(r,t) = \frac{1}{2}(\Phi - \Phi^s(r,t,G\Phi))^t R_{nn}(\Phi - \Phi^s(r,t,G\Phi)) \quad (37)$$

In order to find r and t which minimize the above expression, various well-known nonlinear optimization algorithms can be applied. Since the evaluation function expressed by the above expression had a large number of local minimums, the evaluation function is preferably optimized by using a simulated annealing method which seems to be strong against a problem having a large number of local minimums or using a genetic algorithm. The following method is also preferably used. That is, the optimization expressed by the above expression is divided into two steps, i.e., the step of fixing the profile t to perform optimization related to the position r and the step of optimizing the profile t, a general nonlinear optimization algorithm such as a quasi-Newton method or a conjugate gradient method is applied to the first step, and the simulated annealing method or the genetic algorithm is applied to the step of optimizing the profile t.

As described above, according to the fourth embodiment, since a plurality of samples are used as the measurement values of a magnetic field distribution used for estimation, an amount of information which can be used to estimate current dipoles becomes large, and an increase in the number of parameters related to the plurality of current dipoles to be estimated is not larger than the increase in the amount of information. For this reason, the positions, directions, magnitudes of the current dipoles and changes in magnitude of the current dipoles with time can be estimated stably more than in the prior art.

Figure 9:
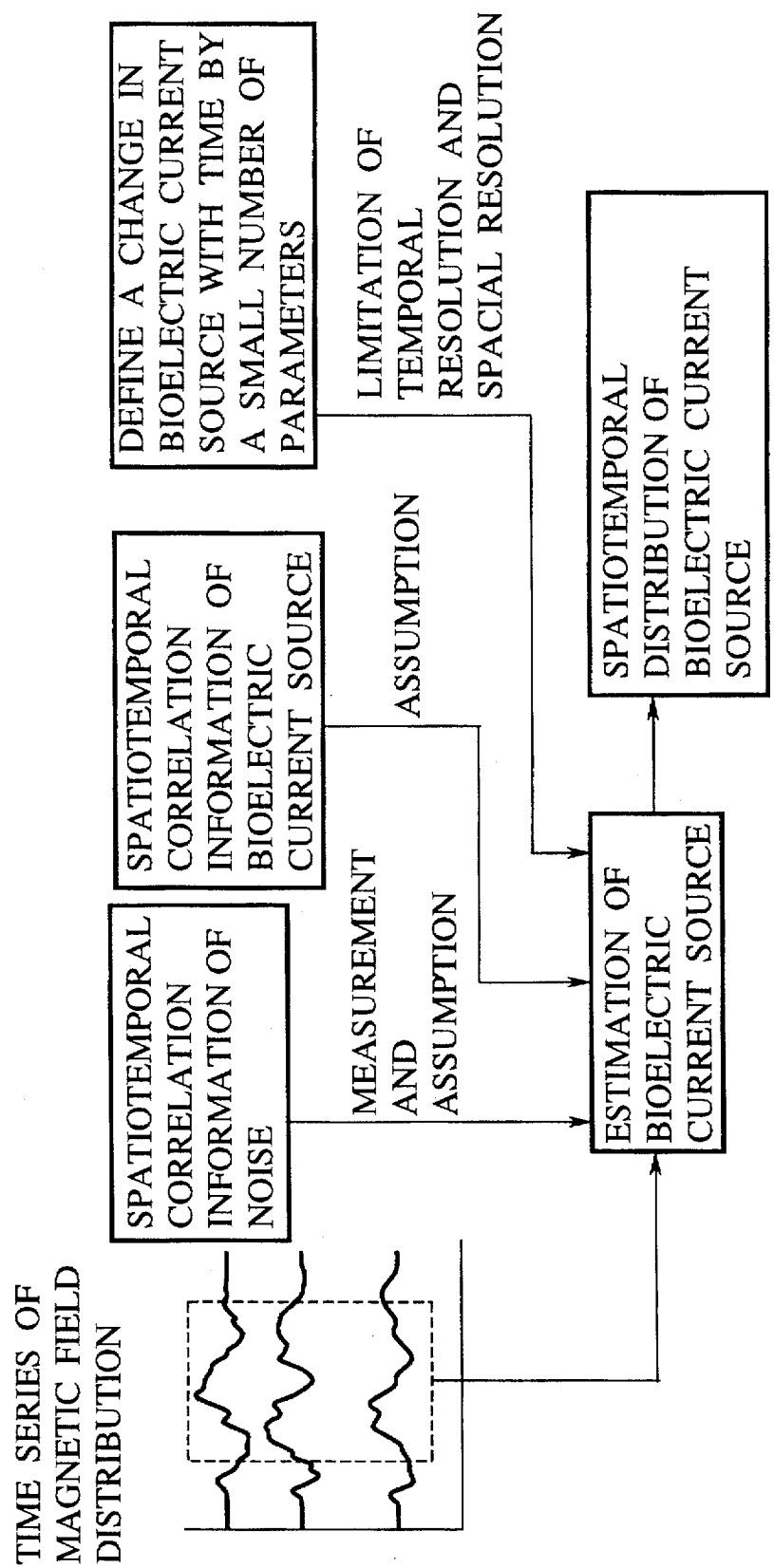
FIG. 9 is a conceptual view showing the fifth embodiment in a method of estimating a bioelectric current source according to the present invention.

The fifth embodiment in a method of estimating a bioelectric current source according to the present invention will be described below. FIG. 9 is a conceptual view of the fifth embodiment. According to this embodiment, a large number of evaluation points are set in a target region of an organism, and it is assumed that current dipoles are respectively present at the evaluation points. A change in a current dipole moment at each evaluation point with time is estimated on the basis of the measurement value of the time series in a period of time of the magnetic distribution, and a change in each component of the current dipole moment at each evaluation point with time is expressed by parameters which are smaller in number than the samples of the measurement values. As a result, the temporal resolution of the estimated current dipoles is limited. However, the number of parameters to be estimated can be reduced, the estimation values can be stably obtained.

Figure 10:
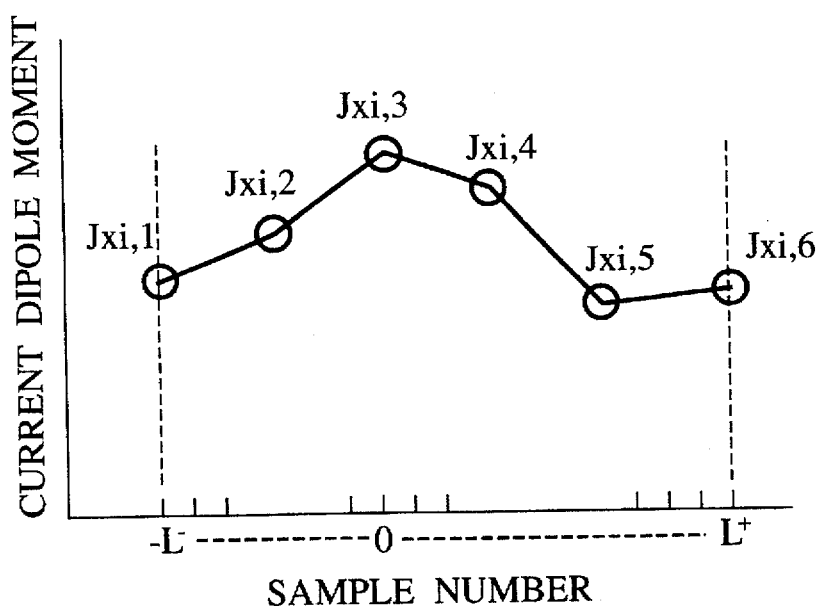
FIG. 10 is a graph showing a change in x component of a current dipole moment with time.

One method of expressing changes in current dipole moment with time by using a small number of parameters will be described below. A temporal waveform between L samples of an x component of the current dipole moment at the ith evaluation point of N evaluation points set in the target region of the organism is expressed by parameters which are H in number as shown in FIG. 10. Referring to FIG. 10, in order to express a change in dipole moment at the ith evaluation point with time in a period of time between the samples having sample numbers L (from $-L^-$ to $L^+$) of the measurement data of the magnetic field distribution, H (6 in FIG. 10) times are set (at equal intervals in FIG. 10), values $Jx_{i,1}, \ldots, J_{xi,H}$ of the x component of the dipole moment at this point are used as parameters. It is assumed that the dipole moment between the samples linearly changes. As another method, a method such as a cubic spline interpolation method can be used. Similarly, the y and z components of the dipole moment are respectively expressed by H parameters $J_{yi,1}, \ldots, J_{yi,H}$ and H parameters $J_{zi,1}, J_{zi,H}$. A vector obtained by vertically arranging the total of 3 H parameters $J_{yi,j}, J_{yi,j},$ and $J_{zi,j}$ such that j changes from 1 to H is represented by $J_i$. The vector $J_i$ expresses a change dipole moment at the ith evaluation point with time. A vector J obtained by vertically arranging vectors $J_i$ such that i changes from 1 to N expresses the temporal waveform of a dipole distribution in the organism in a period of time corresponding to the L samples of magnetic field distribution measurement data. Since the linear relation between a theoretical value Φ' of the time series of the magnetic field distribution and the temporal waveform J of the dipole distribution is established, this relation can be expressed as follows:

$$\Phi' = DJ \quad (38)$$

where D is an LM×3HN matrix.

At this time, the temporal waveform J of a dipole distribution which minimize the square error between the measurement data Φ and theoretical value Φ' of the magnetic field distribution is estimated by using the Moor-Penrose general inverse matrix $D^+$ of the matrix D as follows:

$$J = D^+ \Phi' \quad (39)$$

Also, a correlation matrix $R_{JJ}$ and a noise correlation matrix $R_{nn}$ of the current sources can be designated to limited to the spatial resolution of the current source distribution. The distance between the ith and jth evaluation points of a large number (N) of evaluation points set in the target region of the organism is represented by $d_{i,j}$. The correlation matrix $R_{JJ}$ of the current sources with considering as to both temporal and spatial directions is corrected as follows:

$$R_{JJ} = (JJ^t) = \begin{pmatrix} s(d_{1,1})I_{3H} & \cdots & s(d_{1,M})I_{3H} \\ \cdot & & \cdot \\ \cdot & & \cdot \\ \cdot & & \cdot \\ s(d_{N,1})I_{3H} & \cdots & s(d_{N,M})I_{3H} \end{pmatrix} \quad (40)$$

where $I_{3H}$ is a 3 H-dimensional unit matrix, $d_{i,j}$ is the distance between the ith and jth evaluation points, and a function s(x) is a function expressed by the following expression:

$$s(x) = a^2 \frac{\sin(2\pi f_x x)}{2\pi f_x x} \quad (41)$$

where a is a constant related to an amplitude. In this case, the representative magnitude of a dipole moment is given as the value of a.

By using the correlation matrix $R_{JJ}$ of the current sources obtained as described above and the noise correlation matrix used $R_{nn}$ in the third embodiment, the temporal waveform J of the dipole distribution is estimated as follows:

$$J = R_{JJ} D^t (DR_{JJ} D^t + R_{nn})^{-1} \Phi \quad (42)$$

As described above, according to the fifth embodiment, since a plurality of samples are used as the measurement data of a magnetic field distribution used for estimation, an amount of information which can be used to estimate a current source distribution becomes large, and an increase in the number of parameters the temporal waveform of the current source distribution to be estimated is not larger than the increase in the amount of information. For this reason, the current source distribution can be estimated stably more than in the prior art.

The sixth embodiment in a method of estimating a bioelectric current source according to the present invention. This embodiment is a modification of the first embodiment. According to the sixth embodiment, when the estimation value of a magnetic field distribution (true magnetic field distribution from which noise is removed) at time of interest is to be calculated, in addition to the measurement data of the sample at time of interest of biomagnetic field measurement data to which noise is added and the measurement data of several samples at times after and before the time of interest, the measurement data of a sample at time of interest of the multi-channel measurement data having bioelectric potential such as brain waves, an electrocardiogram, an electromyogram, a magneto-oculogram, and the like to which noise is added and the measurement data of several samples at times before and after the time of interest can also be used.

More specifically, an M'-channel measurement value of a bioelectric potential is added to the jth measurement value $\Phi_{i,j}$ of the ith channel of the magnetic distribution measured at the number M of channels to obtain the measurement data of all the M+M' channels. The measurement data is regarded as new M-channel measurement data. Thereafter, the true values of a biomagnetic field and a bioelectric potential are estimated by the method described in the first embodiment. If necessary, by using the estimation result, a bioelectric current source is estimated.

According to this embodiment, in order to remove the noise of a biomagnetic field, in addition to the spatiotemporal correlation information of the measured biomagnetic field, spatiotemporal correlation information between a bioelectric potential (e.g., an electrocardiogram or an electro-oculogram) and a biomagnetic field is used. For this reason, noise mixed in the biomagnetic field due to action of a heart or motion of eyes can be removed, and the noise removal efficiency of the biomagnetic field is considerably improved. Therefore, when the bioelectric current source is estimated on the basis of the biomagnetic field from which noise is removed as described above, an estimation error of the bioelectric current source caused by motions of a heart, eyes, a hand, or a leg can be reduced. In particular, this embodiment can perform measurement of a biomagnetic field with moving eyes, a hand, or a leg which cannot be performed in the prior art.

According to the first embodiment, in order to remove noise added to a measured biomagnetic field, prior to measurement of the biomagnetic field, or after the measurement, noise is measured. However, in each of the third, fourth, and fifth embodiments, as in the first embodiment, the measured noise data can be used to estimate a bioelectric current source. Another example of timing of noise measurement and another example of method of obtaining spatiotemporal correlation information $R_I^{ni,j}$ of noise used in various types of estimation of the present invention on the basis of measured noise data will be described below.

FIG. 11 shows another timing of noise measurement. In a state wherein a patient is set in the apparatus, before or after measurement of the biomagnetic field, and during the measurement of the biomagnetic field, a noise magnetic field is measured once or a plurality of times while the measurement of the biomagnetic field is temporarily stopped. Either the measurement of the noise magnetic field before and after the measurement of the biomagnetic field or the measurement of the noise magnetic field during the measurement of the biomagnetic field may be enough. However, the measurement of the noise magnetic field before and after the measurement of the biomagnetic field is preferably performed. In the measurement of the biomagnetic field, a stimulus signal such as a visual stimulus, a sound stimulus, or a mechanical stimulus or a task such as moving fingers or pushing a button is given to the patient, or an epileptic spike is activated to induce a target signal. When a stimulus or a task need not be provided in measurement of the epileptic spike, after the measurement of the magnetic field or during the measurement of the magnetic field, a noise measurement phase and a biomagnetic field measurement phase are manually specified or automatically specified such that the epileptic spike is automatically determined if possible.

Spatiotemporal correlation information $R_I^{ni,j}$ are obtained on the basis of the noise measurement data in noise measurement phases by the method described in the first embodiment. When the various types of estimation described in the first, third, fourth, and fifth embodiments are performed, correlation information $R_I^{ni,j}$ particularly obtained on the basis of noise measurement phases which are close to each other in time are preferably used instead of that, the correlation information $R_I^{ni,j}$ of the phases are interpolated or extrapolated in the temporal direction to obtain correlation information $R_I^{ni,j}$ on an arbitrary time phase, and the interpolated or extrapolated correlation information $R_I^{ni,j}$ can also be used in the various types of estimation described in the first, third, fourth, and fifth embodiments. As an interpolation method and an extrapolation method, well-known methods may be used. For example, an interpolation method using linear interpolation, spline interpolation, Lagrange's interpolation, or the like can be used.

As has been described above, according to the present invention, a current source distribution and a current dipole can be estimated at a high accuracy.

It should be understood that many modifications and adaptations of the invention will become apparent to those skilled in the art and it is intended to encompass such obvious modifications and changes in the scope of the claims appended hereto.

What is claimed is:

1. A method of estimating a bioelectric current source in which a plurality of magnetic field measurement means are arranged near a subject, comprising the steps of measuring spatiotemporal magnetic field distribution data within a first predetermined period of time by the plurality of magnetic field measurement means;

calculating matrix data of temporal correlation and spatial correlation of said spatiotemporal magnetic distribution data within the first predetermined period of time;

measuring spatiotemporal magnetic field distribution data within a second predetermined period of time by the plurality of magnetic field measurement means;

acquiring spatiotemporal magnetic field distribution without noise within the second predetermined period of time on the basis of said spatiotemporal magnetic field distribution data within the second predetermined period of time and the matrix data of temporal correlation and spatial correlation of said spatiotemporal magnetic distribution data within the first predetermined period of time; and estimating a current distribution and/or at least one current dipole at a desired time within the second predetermined period of time by using magnetic field distribution at the desired time of the spatiotemporal magnetic field distribution without noise within the second predetermined period of time.

2. A method of estimating a bioelectric current source according to claim 1, further comprising:

measuring spatiotemporal magnetic field distribution data within a third predetermined period of time by the plurality of magnetic field measurement means; and calculating matrix data of temporal correlation and spatial correlation of noise data included in said spatiotemporal magnetic distribution data within the third predetermined period of time; wherein the matrix data of temporal correlation and spatial correlation of noise data is also used to estimate the current distribution and/or at least the one current dipole.

3. A method of estimating a bioelectric current source according to claim 2, wherein the current distribution and/or the current dipole are/is estimated by:

measuring the noise data of M channels in a state wherein the patient is not set on a measurement table .or in a state wherein the patient is set on the measurement table but a stimulus or a task is not given to the patient in measurement of an induced magnetic field;

setting ith-channel data and jth-channel data of the noise data to be $a_h$ and $b_h$, respectively;

calculating $D[a_h]D^*[b_h]$ of all combinations by using a fast Fourier transform algorithm;

obtaining cross-correlation information $R_I^{ni,j}$ of the noise data by performing discrete inverse Fourier transform to a value obtained by modeling a calculation result of $D[a_h]D^*[b_h]$ with a smooth curve by means of the fast Fourier transform algorithm;

measuring the spatiotemporal magnetic field distribution data of the M channels with setting the patient on the measurement table;

extracting L data from the spatiotemporal magnetic field distribution data in time and setting the ith-channel data and the jth-channel data of the L data to be $a_h$ and $b_h$, respectively;

calculating $D[a_h]D^*[b_h]$ of all the combinations by using the fast Fourier transform algorithm;

obtaining cross-correlation information $R_l^{i,j}$ of the spatiotemporal magnetic field distribution data by performing the discrete inverse Fourier transform to the value obtained by modeling the calculation result of $D[a_h]D^*[b_h]$ with a smooth curve by means of the fast Fourier transform algorithm;

obtaining cross-correlation information $R_l^{si,j}$ of true spatiotemporal magnetic field distribution data by subtracting $R_l^{ni,j}$ from $R_l^{i,j}$;

constituting $<\Phi_{i,0}{}^s \Phi_s{}^t>$ on the basis of the following two expressions;

$$(\Phi_{i,0}^s\Phi_s^t) = ((\Phi_{i,0}^s\Phi_1^t)\ldots(\Phi_{i,0}^s\Phi_M^t))$$

$$(\Phi_{i,0}^s\Phi_l^t) = (R_L^{sij}\ldots R_{L+l}^{sij})$$

constituting $<\Phi \ \Phi^t>$ on the basis of the following two expressions;

$$(\Phi\Phi^t) = \left(\begin{pmatrix}\Phi_1 \\ \cdot \\ \cdot \\ \cdot \\ \Phi_M\end{pmatrix}(\Phi_1^t\ldots\Phi_M^t)\right) = \begin{pmatrix}(\Phi_1\Phi_1^t) & \cdots & (\Phi_1\Phi_M^t) \\ \cdot & & \cdot \\ \cdot & & \cdot \\ \cdot & & \cdot \\ (\Phi_M\Phi_1^t) & \cdots & (\Phi_M\Phi_M^t)\end{pmatrix}$$

$$(\Phi_i\Phi_j^t) = \begin{pmatrix}R_0^{ij} & R_1^{ij} & \cdots & R_L^{ij} \\ R_1^{ij} & R_0^{ij} & & \\ \cdot & & & \cdot \\ \cdot & & & \cdot \\ \cdot & & & \cdot \\ R_L^{ij} & & \cdots & R_0^{ij}\end{pmatrix}$$

calculating an estimation matrix $<\Phi_{i,0}{}^s \Phi_s{}^t><\Phi \ \Phi^t>^{-1}$; and calculating true magnetic field distribution data at the desired time on the basis of an expression $L_{i,0}=<\Phi_{i,0}{}^s \Phi_s{}^t><\Phi \ \Phi^t>^{-1}$.

4. A method of estimating a bioelectric current source in which a plurality of magnetic field measurement means are arranged near a subject, comprising the steps of:

measuring spatiotemporal magnetic field distribution data together with bioelectric potential data within a first predetermined period of time by the plurality of magnetic field measurement means;

calculating matrix data of temporal correlation and spatial correlation of said spatiotemporal magnetic distribution data together with the bioelectric potential data within the first predetermined period of time;

measuring spatiotemporal magnetic field distribution data together with bioelectric potential data within a second predetermined period of time by the plurality of magnetic field measurement means;

acquiring spatiotemporal magnetic field distribution together with the bioelectric potential data without noise within the second predetermined period of time on the basis of said spatiotemporal magnetic field distribution data together with the bioelectric potential data within the second predetermined period of time and the matrix data of temporal correlation and spatial correlation of said spatiotemporal magnetic distribution data together with the bioelectric potential data within the first predetermined period of time; and estimating a current distribution and/or at least one current dipole at a desired time within the second predetermined period of time by using magnetic field distribution at the desired time of the spatiotemporal magnetic field distribution together with the bioelectric potential data without noise within the second predetermined period of time.

5. A method of estimating a bioelectric current source in which a plurality of magnetic field measurement means are arranged near a subject, comprising the steps of:

measuring spatiotemporal magnetic field distribution data within a predetermined period of time;

calculating matrix data of temporal correlation and spatial correlation of a bioelectric current source in the subject by using said spatiotemporal magnetic field distribution data; and estimating a current distribution and/or at least one current dipole at a desired time by using magnetic field distribution at the desired time of said spatiotemporal magnetic field distribution and the matrix data of temporal correlation and spatial correlation of a bioelectric current source in the subject.

6. A method of estimating a bioelectric current source in which a plurality of magnetic field measurement means are arranged near a subject, comprising the steps of:

measuring spatiotemporal magnetic field distribution data together with bioelectric potential data within a predetermined period of time;

calculating matrix data of temporal correlation and spatial correlation of a bioelectric current source in the subject by using said spatiotemporal magnetic field distribution data together with the bioelectric potential data; and estimating a current distribution and/or at least one current dipole at a desired time by using magnetic field distribution data together with bioelectric potential data at the desired time and the matrix data of temporal correlation and spatial correlation of a bioelectric current source in the subject.

7. A method of estimating a bioelectric current source in which a plurality of magnetic field measurement means are arranged near a subject, comprising the steps of measuring spatiotemporal magnetic field distribution data within a first predetermined period of time by the plurality of magnetic field measurement means;

calculating matrix data of temporal correlation and spatial correlation of a bioelectric current source in the subject by using said plurality of magnetic field distribution data; measuring spatiotemporal magnetic field distribution data within a second predetermined period of time by the plurality of magnetic field measurement means; and estimating spatiotemporal current distributions within the second predetermined period of time on the basis of the matrix data of the temporal correlation and the spatial correlation of the bioelectric current source and the spatiotemporal magnetic field distribution data within the second predetermined period of time.

8. A method of estimating a bioelectric current source according to claim 7, further comprising:

measuring spatiotemporal magnetic field distribution data within a third predetermined period of time by the plurality of magnetic field measurement means; and calculating matrix data of temporal correlation and spatial correlation of noise data included in said spatiotemporal magnetic distribution data within the third predetermined period of time; wherein the matrix data of temporal correlation and spatial correlation of noise data is also used to estimate the spatiotemporal current distributions within the third predetermined period of time.

9. A method of estimating a bioelectric current source in which a plurality of magnetic field measurement means are arranged near a subject, comprising the steps of:

measuring spatiotemporal magnetic field distribution data together with bioelectric potential data within a first predetermined period of time by the plurality of magnetic field measurement means;

calculating matrix data of temporal correlation and spatial correlation of a bioelectric current source in the subject by using said plurality of magnetic field distribution data together with the bioelectric potential data;

measuring spatiotemporal magnetic field distribution data together with bioelectric potential data within a second predetermined period of time by the plurality of magnetic field measurement means; and estimating spatiotemporal current distributions within the second predetermined period of time on the basis of the matrix data of the temporal correlation and the spatial correlation of the bioelectric current source and the spatiotemporal magnetic field distribution data together with the bioelectric potential data within the second predetermined period of time.

10. A method of estimating a bioelectric current source in which a plurality of magnetic field measurement means are arranged near a subject, comprising the steps of:

acquiring matrix data of temporal correlation and spatial correlation of a bioelectric current source in the subject by using spatial resolution and temporal resolution of a bioelectric current source in a designated area in the subject;

measuring spatiotemporal magnetic field distribution data within a second predetermined period of time by the plurality of magnetic field measurement means; and estimating spatiotemporal current distributions within the second predetermined period of time on the basis of the matrix data of the temporal correlation and the spatial correlation of the bioelectric current source and the spatiotemporal magnetic field distribution data within the second predetermined period of time.

11. A method of estimating a bioelectric current source according to claim 10, further comprising:

measuring spatiotemporal magnetic field distribution data within a third predetermined period of time by the plurality of magnetic field measurement means; and calculating matrix data of temporal correlation and spatial correlation of noise data included in said spatiotemporal magnetic distribution data within the third predetermined period of time; wherein the matrix data of temporal correlation and spatial correlation of noise data is also used to estimate the spatiotemporal current distributions within the third predetermined period of time.

12. A method of estimating a bioelectric current source in which a plurality of magnetic field measurement means are arranged near a subject, comprising the steps of:

acquiring matrix data of temporal correlation and spatial correlation of a bioelectric current source in the subject by using spatial resolution and temporal resolution of a bioelectric current source in a designated area in the subject;

measuring spatiotemporal magnetic field distribution data together with bioelectric potential data within a second predetermined period of time by the plurality of magnetic field measurement means; and estimating spatiotemporal current distributions within the second predetermined period of time on the basis of the matrix data of the temporal correlation and the spatial correlation of the bioelectric current source and the spatiotemporal magnetic field distribution data together with the bioelectric potential data within the second predetermined period of time.

13. A method of estimating a bioelectric current source in which a plurality of magnetic field measurement means are arranged near a subject, comprising the steps of:

measuring spatiotemporal magnetic field distribution data at times of N within a predetermined period of time by the plurality of magnetic field measurement means;

assuming a change with time of the magnitude of at least one current dipole which the position and the direction thereof are fixed within the predetermined period of time as at least one reference waveform defined by parameters smaller in number than N;

calculating spatiotemporal magnetic field distribution data within the predetermined period of time on the basis of the parameters;

updating the position and the direction of at least the one current dipole and said calculated spatiotemporal magnetic field distribution data;

repeating above two steps until a difference between said measured spatiotemporal magnetic field distribution data within the predetermined period of time and said calculated spatiotemporal magnetic field distribution data converges within a predetermined value; and displaying at least the updated position of at least the one current dipole.

14. A method of estimating a bioelectric current source according to claim 13, further comprising:

measuring spatiotemporal magnetic field distribution data within a second predetermined period of time by the plurality of magnetic field measurement means; and calculating matrix data of temporal correlation and spatial correlation of noise data included in said spatiotemporal magnetic distribution data within the second predetermined period of time; wherein the matrix data of temporal correlation and spatial correlation of noise data is also used to update the position and the direction of at least the one current dipole.

15. A method of estimating a bioelectric current source according to claim 14, wherein the parameters are also updated on the basis of said measured spatiotemporal magnetic field distribution data and said calculated spatiotemporal magnetic field distribution data within the predetermined period of time.

16. A method of estimating a bioelectric current source according to claim 13, wherein the parameters are also updated on the basis of said measured spatiotemporal magnetic field distribution data and said calculated spatiotemporal magnetic field distribution data within the predetermined period of time.

17. A method of estimating a bioelectric current source in which a plurality of magnetic field measurement means are arranged near a subject, comprising the steps of:

measuring spatiotemporal magnetic field distribution data together with bioelectric potential data at times of N within a predetermined period of time by the plurality of magnetic field measurement means;

assuming a change with time of the magnitude of at least one current dipole which the position and the direction thereof are fixed within the predetermined period of time as at least one reference waveform defined by parameters smaller in number than N;

calculating spatiotemporal magnetic field distribution data within the predetermined period of time on the basis of the parameters;

updating the position and the direction of at least the one current dipole and said calculated spatiotemporal magnetic field distribution data;

repeating above two steps until a difference between said measured spatiotemporal magnetic field distribution data together with the bioelectric potential data within the predetermined period of time and said calculated spatiotemporal magnetic field distribution data converges within a predetermined value; and displaying at least the updated position of at least the one current dipole.

18. A method of estimating a bioelectric current source in which a plurality of magnetic field measurement means are arranged near a subject, comprising the steps of:

measuring spatiotemporal magnetic field distribution data at times of N within a predetermined period of time by the plurality of magnetic field measurement means;

assuming a change with time of the magnitude or the magnitude and the direction of at least one current dipole which the position and the direction thereof are fixed within the predetermined period of time as at least one reference waveform defined by parameters smaller in number than N;

estimating the parameters on the basis of said measured spatiotemporal magnetic field distribution data within the predetermined period of time;

acquiring the amplitude or the amplitude and the direction of at least the one current dipole within the predetermined period of time on the basis of the estimated parameters; and displaying the magnitude or the magnitude and the direction of at least the one current dipole.

19. A method of estimating a bioelectric current source according to claim 18, further comprising:

measuring spatiotemporal magnetic field distribution data within a second predetermined period of time by the plurality of magnetic field measurement means; and calculating matrix data of temporal correlation and spatial correlation of noise data included in said spatiotemporal magnetic distribution data within the second predetermined period of time; wherein the matrix data of temporal correlation and spatial correlation of noise data is also used to estimate the parameters.

20. A method of estimating a bioelectric current source according to any one of claims 2, 8, 11, 14 and 19, wherein:

said matrix data of temporal cross-correlation and spatial cross-correlation of noise data measured by said plurality of magnetic field measurement means is measured before and/or after measurement of the magnetic field distribution.

21. A method of estimating a bioelectric current source according to any one of claims 1, 8, 11, 14 and 19, wherein:

said matrix data of temporal cross-correlation and spatial cross-correlation of noise data measured by said plurality of magnetic field measurement means is measured at each time at which a stimulus signal and a task are not provided during measurement of the magnetic field distribution.

22. A method of estimating a bioelectric current source according to claim 21, wherein:

the current distribution or the current dipole at desired time within a predetermined period of time is estimated by using noise data obtained by interpolating or extrapolating each noise data measured at each time at which the stimulus signal and the task are not provided.

23. A method of estimating a bioelectric current source in which a plurality of magnetic field measurement means are arranged near a subject, comprising the steps of:

measuring spatiotemporal magnetic field distribution data together with bioelectric potential data at times of N within a predetermined period of time by the plurality of magnetic field measurement means;

assuming a change with time of the magnitude or the magnitude and the direction of at least one current dipole which the position and the direction thereof are fixed within the predetermined period of time as at least one reference waveform defined by parameters smaller in number than N;

estimating the parameters on the basis of said measured spatiotemporal magnetic field distribution data together with the bioelectric potential data within the predetermined period of time;

acquiring the amplitude or the amplitude and the direction of at least the one current dipole within the predetermined period of time on the basis of the estimated parameters; and displaying the magnitude or the magnitude and the direction of at least the one current dipole.

* * * * *